United States Patent [19]

Abushanab et al.

[11] Patent Number: 5,077,403
[45] Date of Patent: Dec. 31, 1991

[54] PROCESS TO PREPARE PYRIMIDINE NUCLEOSIDES

[75] Inventors: Elie Abushanab, Peacedale; Chandra Vargeese, Kingston, both of R.I.

[73] Assignee: The Board of Governors for Higher Education, State of Rhode Island and Providence Plantations, Providence, R.I.

[21] Appl. No.: 568,412

[22] Filed: Aug. 16, 1990

[51] Int. Cl.$^5$ .............................................. C07D 498/16
[52] U.S. Cl. ...................................... 544/246; 544/247
[58] Field of Search ................................... 544/246, 247

[56] References Cited

PUBLICATIONS

Hall, Charles M., et al., "The Synthesis of $O^2,2$ -Anhydro-5, 6-dihydro Nucleosides", J. Org. Chem. vol. 37, No. 21, 1972, pp. 3290-3293.
Hall et al., J. Org. Chem., vol. 37, No. 21, 1972 pp. 3290-3293.
Ryuzi et al., Chemical Abstract vol. 69, 1968; 524502.

Primary Examiner—Mukund J. Shah
Assistant Examiner—Yogendra N. Gupta
Attorney, Agent, or Firm—Samuels, Gauthier & Stevens

[57] ABSTRACT

A process for the production of a compound of the formula

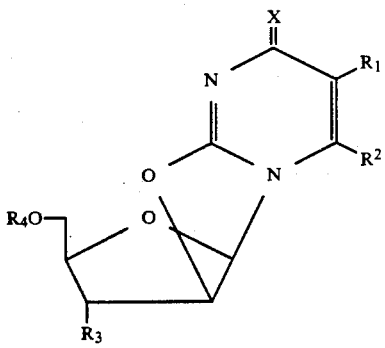

I where $R_1$ and $R_2$ each are alkyl $C_1$-$C_{16}$, aryl, aralkyl, alkenyl, alkynyl, cyano, carboxy and esters, carboximido, N-monosubstituted and N,N-disubstituted carboximido with alkyl, aralkyl, and aryl groups; $R_3$ is tertiary butyldimethyl silyl, $R_4$ is tertiarybutyldimethylsilyl, trimethylsilyl, X=O or NH comprising condensing a compound of the formula

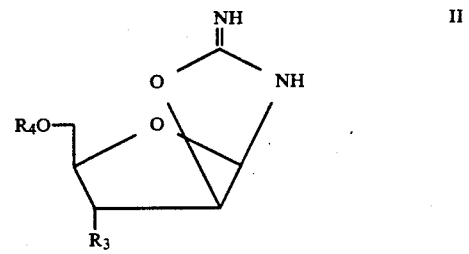

II wherein $R_3$ and $R_4$ are as defined above with a compound of either the formula:

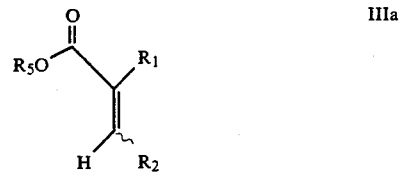

IIIa

OR

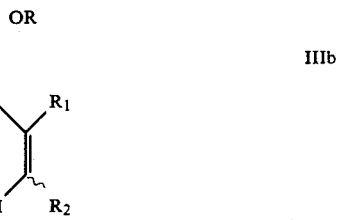

IIIb wherein $R_1$ and $R_2$ are as defined above and $R_5$ is $C_1$-$C_4$; in the presence of a reaction-inert solvent at a temperature of from 50° to about 150° C. forming an intermediate and oxidizing the intermediate product, to form the desired compound of formula I. The products are antiviral.

5 Claims, No Drawings

PROCESS TO PREPARE PYRIMIDINE NUCLEOSIDES

BACKGROUND AND BRIEF SUMMARY OF THE INVENTION

Pyrimidine nucleosides are important antiviral agents, increased attention has recently been focussed on these compounds with the FDA approval of 3'-azido-2',3'-dideoxythymidine (AZT) as an effective treatment for Acquired Immunodeficiency Syndrome (AIDS). Since the synthesis of AZT utilizes the pyrimidine nucleoside β-thymidine as a starting material, new methods for the low-cost production of this and other synthetic intermediates are also becoming important. The present invention involves an expeditious route to the $O^2,2'$-anhydro-1-(β-D-arabinofuranosyl)pyrimidine nucleosides, a class of compounds easily converted to the β-pyrimidine derivatives. The synthesis of these anhydronucleosides is described in the following publications.

Japanese Kokai No. 81 49 398 laid open on May 2, 1981 refers to the synthesis of acylated arabinofuranosylcyclothymine compounds. The process of the Japanese Kokai requires that the iminoarabino(1 2:4.5) oxazoline acid addition salt be acylated.

In an article appearing in J. Mol. Biol. 1970, 47, 537, the authors describe the use of a readily available amino-oxazoline carbohydrate derivate as a useful precursor to a variety of anhydronucleosides.

In the reference, Kampe, K. D., Justus Leibigs Ana-Chem. 1974, (4), 593-607 (ger), reactions of aminooxazolines with unsaturated esters are disclosed. European Patent Application 0 351 126 discloses a process for the formation of $O^2,2'$-anhydro-1-(β-D-arabinofuranosyl)thymine by reacting 2-amino-β-D-arabinofurano-oxazoline(s) with an alkyl 3-halo or alkoxy-methacrylate derivative.

The present invention is also directed to forming $O^2,2'$-anhydro-1-(β-D-arabinofuranosyl)pyrimidines by condensing 2-amino-β-D-arabinofurano-oxazoline(s) with methyl acrylate and acrylonitrile derivatives.

Our invention differs from the prior art by starting with acrylates or acrylonitriles and related derivatives; compounds that are at a lower oxidation state than other substrates previously used for similar condensations. This results in the formation of 5,6-dihydro pyrimidine nucleoside derivatives which are then oxidized to the required nucleosides in high to excellent yields.

Broadly, the present invention is directed to a process for the production of pyrimidine nucleoside compounds of the formula:

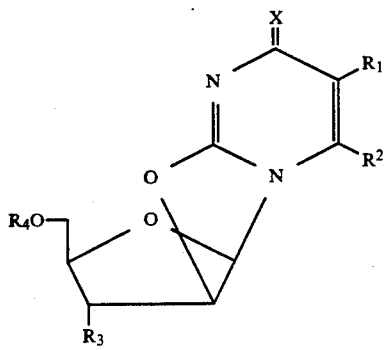

I wherein $R_1$ and $R_2$, each are alkyl $C_1-C_{16}$, substituted alkyl, aryl, substituted aryl, aralkyl, substituted aralkyls, alkenyl, substituted alkenyl, alkynyl, substituted alkynyl, cyano, carboxy, carboxy esters, carboxamido, N-mono substituted and N,N-disubstituted carboxamido with alkyl, aralkyl, and aryl groups. $R_3$ is hydrogen or $OR_4$; $R_4$ is hydrogen, triphenylmethyl, or silyl which is substituted by three substituents selected from $C_1-C_6$ alkyl, phenyl, or combinations thereof; and $X=O$ or NH: comprising condensing a compound of the formula:

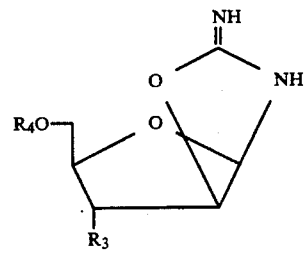

II wherein $R_3$ and $R_4$ are as defined above with a compound of either the formula:

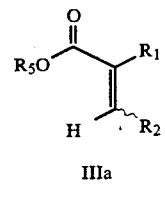

IIIa or

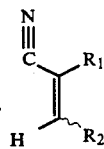

IIIB $R_1$ and $R_2$ are as defined above; and
$R_5$ is $C_1-C_4$ alkyl.

The condensation is in the presence of a reaction inert solvent at a temperature of 50° C. to about 150° C.; to form a compound of the formula:

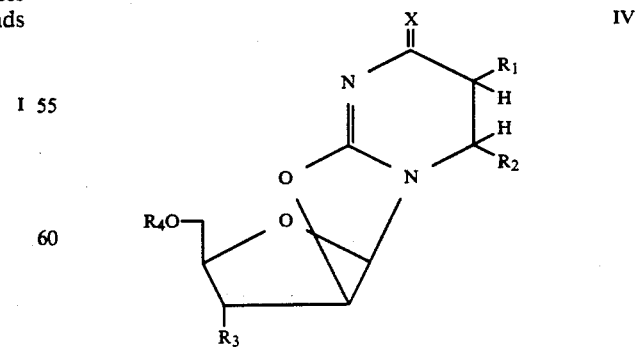

IV wherein $R_1$, $R_2$, $R_3$ and $R_4$ and X are as defined above.
A compound of the formula IV is oxidized to form the compound of formula I.

The present invention is also directed to compounds of formula IV.

DESCRIPTION OF THE PREFERRED EMBODIMENT

Presently there are several methods to produce pyrimidine nucleosides, however these methods are limited in their utility either because they cannot form 5-substituted pyrimidine derivatives directly or involve long synthetic routes resulting in increased costs and reduced yields. With the new process disclosed herein, by condensing a known oxazoline derivative with an acrylate ester a new compound of the formula:

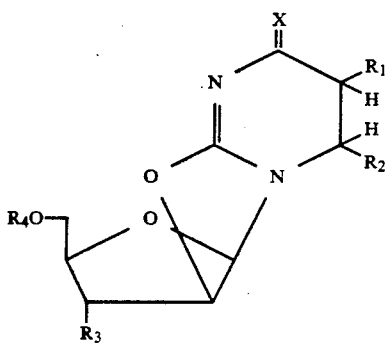

IV has been derived where $R_1$, $R_2$, $R_3$, $R_4$ and X are as defined above. Oxidizing this new compound of the above formula the desired pyrimidine is produced efficiently and in high yields.

The first step process of the present invention comprises the condensation of oxazoline derivatives of formula II with an acrylate ester or acrylonitrile of formula III to yield dihydro derivatives of formula IV. This process is preferably carried out at a temperature of about 50° C. to about 150° C., preferably 80° C. to 100° C., in the presence of a reaction-inert solvent. Preferred solvents are organic solvents such as $C_1$–$C_4$ alkanols, preferably methanol, and other suitable solvents including dimethyl sulfoxide, dimethylformamide, dimethylacetamide, acetone, etc. Water may also be used as a solvent. Although the preferred embodiment employs equimolar amounts of compounds II and III, an excess of either reagent may be used.

In the reaction between the compounds of formula II and formula III, the pressure is not critical. Generally, the reaction is conducted at a pressure of from about 0.5 to about 2.0 atmospheres, preferably at ambient pressure, (i.e. about one atmosphere).

The second step of the process comprises the oxidation of a dihydro derivative formula IV to yield a β-pyrimidine anhydronucleoside of formula I. Preferred oxidizing agents are dichlorodicyanoquine (DDQ), p-chloranil, O-chloranil, N-bromosucinimide (NBS), and N-chlorosucinimide (NCS). This process is preferably carried out at a temperature of from about 50° C. to about 150° C., preferably 80° C. to 100° C.

Two major advantages of this process over those of the prior art are the low cost of the starting compounds and the efficiency of the process and secondly that there are no α-or β- mixtures in the final product, which permits a high yield of the desired compound.

EXAMPLE 1

A suspension of 1.009 g(2.5/mmole) of 2-amino-3',5'-di-t-butyldimethylsilyl-β-D-arabinofurano[1',2':4,5]-2-oxazoline ($R_3$ and $R_4$ are each TBDMS) was reacted with 1.340 ml of 2-methylmethacrylate to yield 3',5'-O-di t-butyl dimethylsilyl-5,6-dihydro-O,-2,2' anhydro β-D-arabinofuranosyl thymine.

The reaction conditions were, heating at 90° C. for at least twelve (12) hours. The residue obtained after the removal of excess methyl methacrylate was isolated by chromotography on silica gel using appropriate mixtures of chloroform:hexane. The yield was 980 mg (79%).

| ANALYSIS | | |
|---|---|---|
| | Theory % | % Found |
| C | 56.13 | 56.29 |
| H | 8.99 | 8.85 |
| N | 5.95 | 5.85 |
| Melting Point = 116–117° C. | | |

| NMR | |
|---|---|
| | δ |
| H-1' | 5.74(d J=5.7) |
| H-2' | 4.97(ddd J=5.7, 1.43, 0.54) |
| H-3' | 4.64(ddd J=2.87, 1.4, 0.58) |
| H-4' | 4.05(dddd, J=0.54, 2.87, 7.72, 4.84) |
| H-5'a+b | 3.63 and 3.49($q_{AB}$J=10.7, 7.77, 4.77) |
| H-6a+b | 3.73 and 3.23($q_{AB}$J=11.9, 7.29, 7.17) |
| H-5 | 2.56(ddq J=7.29, 7.17) |
| CH3 | 1.25(d J=6.97) |
| t-BuSi | 0.90 and 0.88(s, 18H) |
| CH3—Si | 0.13(s, 3H), 0.15(s, 3H), 0.05(s,6H) |

Preferably, $R_3$ and $R_4$ are TBDMS. Although relatively expensive, they are stable and are not cleaved by the methanol produced in the condensation reaction. However, when $R_3$ and $R_4$ are trimethyl silyl (TMS), although less expensive, they are less stable and are cleaved by the methanol. It has been found that if TMS is used, the methanol can be captured with 3 Å molecular sieves.

The addition of the hydroquinone prevents polymerization of the acrylate ester.

EXAMPLE II

Following the procedures of Example 1, 5 grams of the 2-amino-3',5'-O-trimethylsilyl β-D-arabinofurano[1',2':4,5]-2-oxazoline and 15 milliliters of 2-methylmethacrylate were reacted except that this mixture was refluxed for approximately 24 hours. The methylmethacrylate was removed and the product isolated by chromotography on silica gel with appropriate mixtures of chloroform methanol. The yield was 80%.

| ANAYLSIS | | |
|---|---|---|
| | Theory % | % Found |
| C | 49.58 | 49.39 |
| H | 5.83 | 5.79 |
| N | 11.56 | 10.76 |
| Melting point = 196–197° C. | | |

EXAMPLE III

A solution of 100 milligrams of compound of example I (0.213 mmoles in 2 ml dry benzene) was refluxed for 9 hours with dichlorodicyanoquinone to form $O^2,2'$-anhydro-1-(β-D-arabinofuranosyl)thymine. The progress of the reaction was followed by thin layer chromotography which showed the disappearance of the starting compound after 9 hours.

| ANAYLSIS | | |
|---|---|---|
| | Theory % | % Found |
| C | 56.37 | 57.21 |
| H | 8.60 | 8.49 |
| N | 5.98 | 5.79 |
| Melting point = 140–141° C. | | |

| NMR | |
|---|---|
| | δ |
| H-6 | 7.18(q J=1.47) |
| H-1' | 6.10(d J=5.51) |
| H-2' | 5.05(dd J=5.51, 0.73) |
| H-3' | 4.59(dd J=0.73, 2.5) |
| H-4' | 4.12(ddd J=2.50, 4.78, 7.36) |
| [ H-5'$_a$ ] | 3.52 q$_{AB}$ J=11.05 J=4.78 |
| [ H-5'$_b$ ] | 3.33 J =7.36 |
| CH$_3$ | 1.96 d J=1.47 |
| CHBu | 0.89 s 9H |
| | 0.81 s 9H |
| CH$_3$—Si— | 0.03 s 12H |

Although described with reference to β-pyrimidines nucleosides as the starting material, it is within the scope of the invention that α-pyrimidines nucleosides can be prepared following the described procedure.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A process for the production of a compound of the formula:

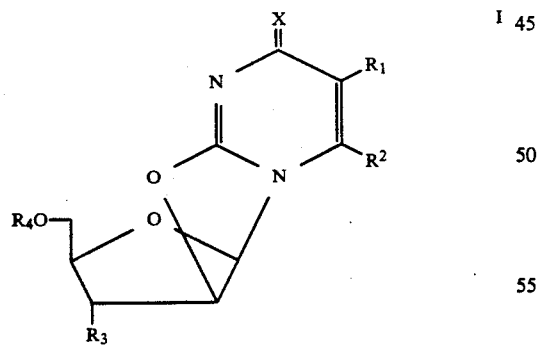

where $R_1$ and $R_2$ each are alkyl $C_1$–$C_{16}$, substituted alkyl, aryl, substituted aryl, aralkyl, substituted aralkyls, alkenyl, substituted alkenyl, alkynyl, substituted alkynyl, cyano, carboxy, carboxy esters, carboxamido, N-mono substituted and N,N-disubstituted carboxamido with alkyl, aralkyl, and aryl groups; $R_3$ is tertiary butyldimethylsilyl or trimethylsilyl; $R_4$ is tertiary butyldimethylsilyl or trimethylsilyl, X=O or NH, comprising condensing a compound of the formula:

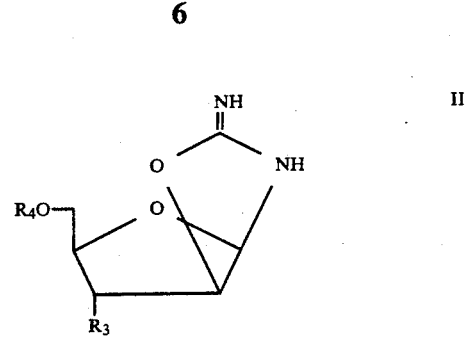

wherein $R_3$ and $R_4$ are as defined above with a compound of either the formula:

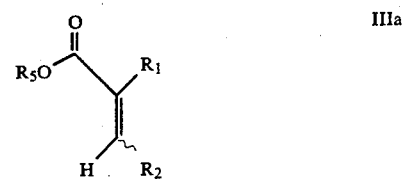

or

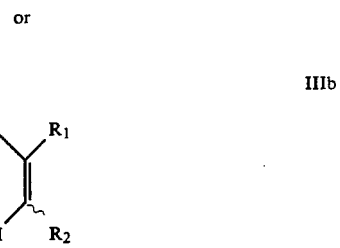

wherein $R_1$ and $R_2$ are as defined above an $R_5$ is $C_1$–$C_4$; in the presence of a reaction-inert solvent at a temperature of from 50° to about 150° C.

forming an intermediate of the formula:

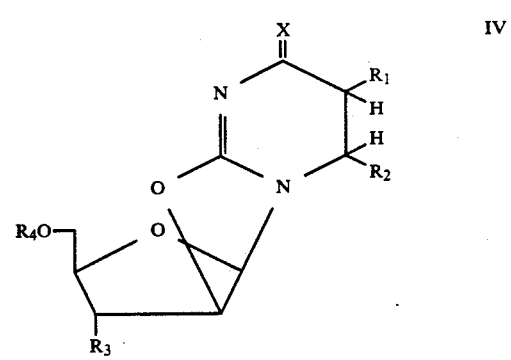

wherein $R_1$, $R_2$, $R_3$ and $R_4$ are as defined above and X is O or NH; and oxidizing the intermediate product, formula IV, to form the desired compound of formula I.

2. A process for the production of a compound of the formula:

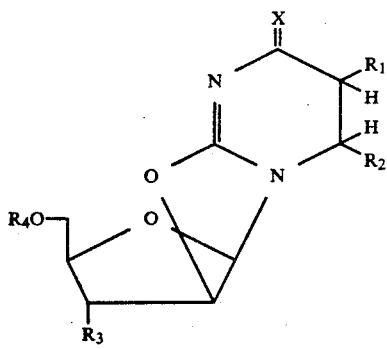

where $R_1$ and $R_2$ each are alkyl $C_1$-$C_{16}$, substituted alkyl, aryl, substituted aryl, aralkyl, substituted aralkyls, alkenyl, substituted alkenyl, alkynyl, substituted alkynyl, cyano, carboxy, carboxy esters, carboxamido, N-mono substituted and N,N-disubstituted carboxamido with alkyl, aralkyl, and aryl groups; $R_3$ is tertiary butyldimethylsilyl or trimethylsilyl; $R_4$ is tertiary butyldimethylsilyl or trimethylsilyl or combinations thereof, X=O or NH, comprising condensing a compound of the formula:

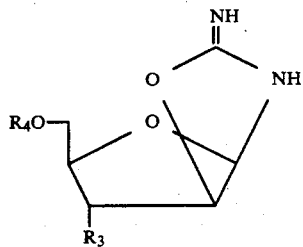

wherein $R_3$ and $R_4$ are as defined above with a compound of either the formula:

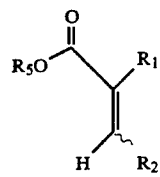

or

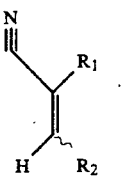

wherein $R_1$ and $R_2$ are as defined above and $R_5$ is $C_1$-$C_4$; in the presence of a reaction-inert solvent at a temperature of from 50° to about 150° C. to form the desired compound of formula IV.

3. The process of claim 1 wherein the condensation step is carried out at about 80° C.

4. The process of claim 2 wherein the condensation step is carried out at about 80° C.

5. The process of claim 1 wherein the oxidizing agent used in the oxidizing step is selected from the group consisting of DDQ, p-chloranil, O-chloranil, NBS and NCS.

* * * * *